United States Patent [19]

Masuda

[11] Patent Number: 5,180,815
[45] Date of Patent: Jan. 19, 1993

[54] MODIFIED PROTEIN FOR CARRYING HAPTEN

[75] Inventor: Nobuhito Masuda, Saitama, Japan

[73] Assignee: Fuji Photo Film Co., Ltd., Kanagawa, Japan

[21] Appl. No.: 880,292

[22] Filed: May 5, 1992

Related U.S. Application Data

[63] Continuation of Ser. No. 336,815, Apr. 12, 1989, abandoned.

[30] Foreign Application Priority Data

| Apr. 13, 1988 | [JP] | Japan | 63-88971 |
| Sep. 13, 1988 | [JP] | Japan | 63-227468 |
| Oct. 20, 1988 | [JP] | Japan | 63-262773 |

[51] Int. Cl.$^5$ ............ C07K 17/02; C07K 15/14; C12N 9/96; A61K 39/385
[52] U.S. Cl. .................. 530/404; 530/363; 530/380; 530/387; 530/403; 530/405; 530/406; 530/408; 530/409; 530/807; 530/389.8; 530/388.9; 424/88; 435/188; 435/961; 435/964; 436/543; 436/823
[58] Field of Search ........... 530/403, 404, 405, 406, 530/408, 409, 363, 387, 380, 807; 424/88; 435/961, 964, 188; 436/543, 823

[56] References Cited

U.S. PATENT DOCUMENTS

| 4,302,386 | 11/1981 | Stevens | 530/322 |
| 4,493,795 | 1/1985 | Nestor, Jr. et al. | 530/326 |

FOREIGN PATENT DOCUMENTS

| 2557458 | 7/1985 | France . |
| 60-42335 | 3/1985 | Japan . |

OTHER PUBLICATIONS

Chu et al (1982) J. Immunol. Methods 55: 73–78.
Erlanger (1980) Methods Enzymol 70: 85–104.
Pesce et al (1986) J. Immunol Methods 87: 21–27.

Primary Examiner—Christine M. Nucker
Assistant Examiner—Kay Kim
Attorney, Agent, or Firm—McAulay Fisher Nissen Goldberg & Kiel

[57] ABSTRACT

Modified proteins for carrying hapten are provided. These carriers are prepared by blocking the amino groups of the original protein and then introducing amino groups into the carboxyl groups of the original protein. The blocking groups may be eliminated at the later stage to regenerate the amino groups of the original protein. The modified protein or polypeptide carrier have the three-dimensional structures different from the original proteins so that they are used in immunoassay while carrying low molecular weight haptens without the fear of forming antibodies for the original proteins. The modified protein carrier may also be used in the passive agglutination immunoassay without the need of absorbing the anti-hapten antibodies by the hapten-carrying carriers.

4 Claims, 2 Drawing Sheets

PROTECTION OF AMINO GROUPS
(STEP 1)

$r \leq p$

AMIDATION OF CARBOXYL GROUPS
(STEP 2)

$2 \leq t \leq s$ (STEP 4)

DEBLOCKING OF PROTECTION GROUPS
(STEP 3)

$h \leq r$ (STEP 5)

$L = L'' - NH_2$

MODIFIED PROTEIN FOR CARRYING HAPTEN

This is a continuation of application Ser. No. 07/336,815, now abandoned, filed Apr. 12, 1989.

BACKGROUND OF THE INVENTION

1. Field of the Invention

The present invention relates to modified proteins or modified polypeptides which are used as carriers for carrying haptens (low molecular weight antigens) for the preparation of hapten antibodies or used as carriers for the preparation of polyvalent hapten antigens used in the immunoassay.

2. Description of Related Art

In the past, antibodies (Ab) for low molecular weight compounds acting as antigens, such as medicines or like chemicals, have been prepared by immunizing the immunorecipient animals with by inoculating conjugates which are prepared by combining these low molecular weight antigens (haptens) or homologues thereof with protein carriers, such as BSA (bovine serum albumin). While the carrier protein has functional groups including amino groups and carboxyl groups, it is considered that hapten molecules combine with the carrier protein at the site of amino or carboxyl groups. Hapten molecules combine more easily with amino groups.

However, all of the amino groups of a protein are not fully combined with hapten molecules to leave the steric structure inherent to the protein at the region where a number of uncombined amino groups are present so that the uncombined amino groups act as antigenic determinants (epitopes; Ag*) for the original protein. Accordingly, an antibody (Ab*) corresponding to the carrier protein is produced in the serum immunized with the protein carrying the hapten. In order to eliminate the influence of Ab*, the prepared anti-hapten anti-serum (Ab) must be absorbed by the carrier (Ag*) per se prior to use.

A similar inconvenience could occur when a hapten-protein conjugate is used in the passive agglutination immunoassay. In the passive agglutination immunoassay, plural mono-epitopic haptens each acting as a monovalent antigen (Ag) are carried by a carrier so that the composite of carrier and plural haptens carried thereby is allowed to act as a polyvalent antigen to cause matrix agglutination due to antigen-antibody binding. The carrier carrying plural hapten antigen (Ag) contacts with anti-hapten antibodies (Ab) so that an antigen-antibody matrix is formed. The amount of the formed matrix is detected by the determination of change in turbidity. When a free monovalent hapten antigen is present, formation of matrix is inhibited leading to reduction in turbidity. The amount of the free hapten antigen, i.e. the amount of the antigen contained in the sample, can be quantitatively determined by the analysis of the reduction in turbidity. Of course, when an antibody (Ab*) for the carrier (Ag*) is present, formation of matrix or agglutination occurs by the formation of Ag*-Ab* complex. Accordingly, it is necessary to absorb the used anti-hapten antibody (Ab) preliminarily by the carrier (Ag*) or to use in the passive agglutination immunoassay a composite which is formed by binding the hapten (Ag) to a carrier different from the carrier (Ag*) used in the immunization step.

One counterplan for obviating such inconvenience is to block all of the amino groups of the protein carrier so that the protein is fully denatured. However, realization of such counterplan is extremely difficult, and a large quantity of hapten is needed if such counterplan is adopted. Accordingly, this counterplan cannot be adopted when the quantity of hapten is small.

On the other hand, when the quantity of hapten is very small or the solubility of hapten in solvents is low to lower than the concentration of available hapten solution, it becomes impossible to introduce the hapten sufficiently into the carrier protein leading to insufficient titer of the resultant antibody. It is, therefore, desirable to increase the sites of the carrier at which hapten molecules are introduced so as to obtain a carrier into which the hapten is introduced at high efficiency.

OBJECTS AND SUMMARY OF THE INVENTION

A first object of this invention is to provide a modified protein for carrying a hapten, the amino groups of the protein being substantially completely modified or denatured to eliminate the possibility of formation of an antibody for the carrier at the subsequent immunization step. The modified protein of the invention may be used in the passive agglutination immunoassay without the need of absorbing the anti-hapten antibody (Ab) by the hapten-carrying carrier (Ag*).

A second important object of this invention is to provide a modified protein for carrying a hapten, the efficiency of introducing the hapten being high without the fear of the formation of antibody for the carrier.

The first object of this invention is achieved by the provision of a modified protein for carrying a hapten represented by the following formula of:

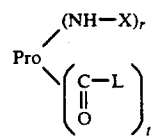

wherein Pro is a protein or a polypeptide; X is an uneliminable or eliminable modifying group for the amino group; L is a modifying group for the carboxyl group having two or more amino groups one of which combines with the carboxyl group of Pro by an amido bond; r is an integer of up to the number of amino groups included in the unmodified Pro; and t is an integer of from 1 to up to the number of carboxyl groups included in the unmodified Pro.

The second object of this invention is achieved by the provision of a modified protein for carrying a hapten represented by the following formula of:

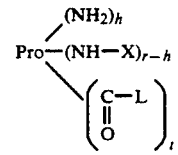

wherein Pro is a protein or a polypeptide; X is an uneliminable or eliminable modifying group for the amino group; L is a modifying group for the carboxyl group having two or more amino groups one of which combines with the carboxyl group of Pro by an amido bond; r is an integer of from 1 to up to the number of amino groups included in the unmodified Pro; h is an integer of from 1 to up to the number of amino groups included in the unmodified Pro; and t is an integer of from 1 to up to the number of carboxyl groups included in the unmodified Pro.

DESCRIPTION OF THE INVENTION

Figure 1A:
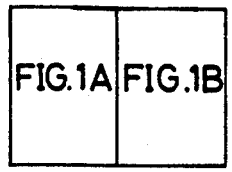
FIGS. 1A and 1B are flow charts showing the process for preparing a modified protein carrier and showing the method of using the modified protein carrier.

The present invention provides a protein or polypeptide carrier having its amino groups blocked by modification and having its carboxyl groups converted to amide forms to introduce new amino groups with which hapten molecules are to be coupled.

By modifying the amino groups with eliminable groups and then eliminating the modifying groups to regenerate the amino groups of the original protein, the efficiency in introducing hapten can be improved by the utilization of the regenerated amino groups and the introduced amino groups.

Protein

Typical examples of the proteins which may be used in this invention include bovine serum albumin (BSA), keyhole limpet hemocyanin (KLH), IgG, ferritin and thyroglobulin. Natural or synthesized polypeptides may be used for the starting materials for the modified protein for carrying a hapten, according to this invention.

Modifying Group X for the Amino Group

Examples of the modifying group for blocking the amino groups of the protein carrier will be set forth below. Eliminable modifying groups are represented by the following formulae of:
—CO—O—R
—SO₂—R
—CO—S—R
—S—R

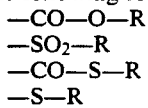

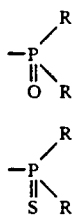

—CO—Y—Z—R
—CHO
—CO—CH₂—COCH₃
—CO—CF₃
—CH₂—C₆H₅
—CH—(C₆H₅)₂
—C—(C₆H₅)₃

In the formulae set forth above, R is a substituted or unsubstituted alkyl, aryl or aralkyl group having 2 to 15 carbon atoms; Y is a substituted or unsubstituted methylene group; and Z is sulfur or oxygen atom.

The modifying groups will be elucidated more specifically. —CO—O—R (Urethane type modifying groups for protecting amino groups)

The urethane type modifying groups for protecting amino groups include alkyloxycarbonyl groups (alkoxycarbonyl groups), aryloxycarbonyl groups and aralkyloxycarbonyl groups, specific examples being t-butoxycalbonyl (Boc), isobutyloxycarbonyl, benzyloxycarbonyl (Z), p-methoxybenzyloxycarbonyl, t-amyloxycarbonyl, d-isobornyloxycarbonyl and adamantyloxycarbonyl. These modifying groups may be partially substituted. For example, a halogen atom, nitro group or methoxy group may be introduced at the para position of benzyloxycarbonyl group.

One example of —SO₂—R (Sulfonyl type modifying groups) is p-toluenesulfonyl (Tosyl) groups represented by the formula

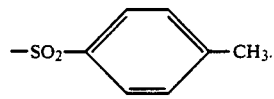

Examples of the modifying groups represented by —CO—S—R are (phenylthio)carbonyl group, (benzylthio)carbonyl group and (butylthio)carbonyl group.

Examples of the modifying groups represented by —S—R (Thio type) are o-nitrophenylthio group and o,p-dinitrophenylthio group.

One example of the modifying groups represented by

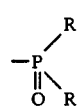

is diphenylphosphonyl (Dpp) group represented by

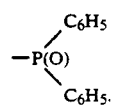

One example of the modifying groups represented by

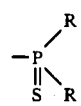

is diphenylphosphinothionyl (Ppt) group represented by

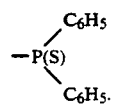

Examples of the modifying groups represented by —CO—Y—Z—R (wherein Y is a substituted or unsubstituted methylene group, and Z is sulfur or oxygen atom) are o-nitrophenoxyacetyl group represented by —CO—CH₂—O—C₆H₅—NO₂, o-nitrophenoxyisopropylcarbonyl group represented by

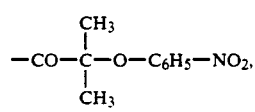

and a group represented by

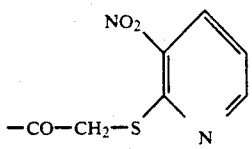

Further examples of the modifying groups for blocking the amino group are formyl group (—CHO), acetoacetyl group (—CO—CH$_2$—COCH$_3$), trifluoroacetyl group (—CO—CF$_3$), benzyl group (—CH$_2$—C$_6$H$_5$), diphenylmethyl group (CH—(C$_6$H$_5$)$_2$), triphenylmethyl (trityl) group (—C—(C$_6$H$_5$)$_3$) and groups represented by

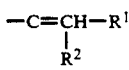

where R$^1$ and R$^2$ each stands for an alkyl group.

Each of the modifying or protection groups described above blocks an amino group of the protein while forming a single bond with the nitrogen atom of the amino group. However, the amino group (—NH$_2$) may also be converted to —N=CH—R so that a double bond is formed with the nitrogen atom of the amino group to block the amino group.

Introduction and elimination of the protection group may be effected by the known method. For instance, an urethane type protection group may be introduced by the isocyanate method, azideformate method, mixed-carbonate method or haloformate method. The protection group may be eliminated, for example, by catalytic hydrogenation, by treating with Na—NH$_3$, by treating with an acid (e.g. hydrogen bromide, trifluoroacetic acid and hydrogen fluoride), by treating with an alkali, and by means of electrolysis or photolysis.

Details of the modifying groups for protecting the amino group and the processes for introducing and eliminating the protection groups are described in the following prior art publications which will be incorporated herein as references.

Izumiya et al., "Principle and Experiment of Peptide Synthesis", Maruzen (1985);

J. P. Greenstein and M. Winitz, "Chemistry of Amino Acids", John Wiley & Sons, New York, Vol II (1961);

E. Schröder, K. Lübke, "The Peptides", Academic Press, New York, Vols. I & II (1965);

M. Bodanszky and M. A. Ondetti, "Peptide synthesis", John Wiley & Sons, New York (1966 & 1976);

"Peptide Chemistry" Series, Proceedings of the Japan symposium on Peptide Chemistry, 1976-1987, Peptide Institute, Protein Research Foundation, Osaka, Japan Examples of uneliminable modifying groups are acyl groups represented by

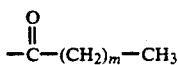

wherein m is an integer of from zero to 4. To ensure that the resultant protein carrier is soluble in water, m should be not more than 4. Acyl group may be introduced by the known technology described in the prior publications.

The number r of the modifying groups X protecting the amino group should be not more than the number p of the amino groups included in the unmodified protein Pro.

Modifying Group L for the Carboxyl Group

It is desirable that the diamine or polyamine for converting the carboxyl group of the carrier protein has 1 to 8 carbon atoms in order to ensure that the resultant modified protein carrier is soluble in water. The space length, i.e. the length between the surface of the carrier and the hapten molecule, may be adjusted by selecting the number of carbon of the diamine or polyamine used for modification. Preferable diamines include, for example, methylenediamine, ethylenediamine and triethylenediamine.

The amino groups included in the polyamine mean not only amino groups corresponding to primary amines (—NH$_2$) but also amino groups corresponding to secondary amines (>NH) which are commonly referred to as amino groups. Accordingly, the terminology "polyamine" used herein is a concept including polyimines having amino groups. The amino group of the modifying group L for modifying the carboxyl group of the carrier protein may be either of primary or secondary amino group which combines with the carboxyl group of the protein through an amide linkage and which is capable of combining with protein.

Examples of preferable polyamine will be set forth below.

Diethylenetriamine   H$_2$N—CH$_2$CH$_2$—NH—CH$_2$CH$_2$—NH$_2$

Triethylenetetramine   H$_2$N—(CH$_2$CH$_2$—NH-)$_2$—CH$_2$CH$_2$—NH$_2$

Tetraethylenepentamine   H$_2$N—(CH$_2$CH$_2$—NH-)$_3$—CH$_2$CH$_2$—NH$_2$

Pentaethylenehaxamine   H$_2$N—(CH$_2$CH$_2$—NH-)$_4$—CH$_2$CH$_2$—NH$_2$

Polyethylenepolyamine   H$_2$N—(CH$_2$CH$_2$—NH-)$_n$—CH$_2$CH$_2$—NH$_2$

Dipropylenetriamine   H$_2$N—CH$_2$CH$_2$CH$_2$—NH—CH$_2$CH$_2$CH$_2$—NH$_2$

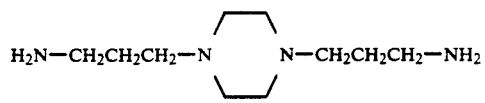

Bis-hexamethylenetriamine   H$_2$N—(CH$_2$)$_6$—NH—(CH$_2$)$_6$—NH$_2$

The carboxyl group of the carrier protein may be converted to amide form by using a polymer of an amino acid (polyamino-acid) having three or more amino groups. Examples of the polyamino-acid which may be used for such purpose include polymers of dimers and trimer of ornithine having α-amino and δ-amino groups, lysine, or oxylysine having α-amino and ε-amino groups. Preferable polyamino-acids acids are lysyllysine which is a dimer of lysine, lysyllysyllysine which is a trimer of lysine and ornithylornithine which is a dimer of ornithine. The number t of amino groups of the carrier protein introduced by the diamine, polyamine or polyamino-acid ranges at least one to the multiplication of the number s of carboxyl group of the original protein Pro. It is desirable that the number of introduced amino groups is generally more than 10, preferably more than 20, in view of the fact that the number of hapten in the hapten-protein conjugate is normally more than 10 molecules/carrier, preferably more than 20 molecules/carrier.

By eliminating substantially all of the modifying groups X bonded to the original amino group, the number of amino groups included in the modified protein carrier is increased by 10 or more, preferably 20 or more, as compared with that in the original protein so that the efficiency for the introduction of hapten is increased correspondingly.

When the carboxyl group of the original protein is converted into amide group using a polyamine or polyamino-acid, the modifying group has two or more amino groups so that the efficiency for the introduction of hapten is further improved since additional hapten molecules may be introduced at the sites provided by the thus introduced amino groups.

When the three-dimensional structure of a high molecular weight molecule, such as a protein or polypeptide, has been once changed by the introduction of modifying groups for protecting the amino groups, the structure is not returned back to the original structure even if the modifying groups are eliminated. Accordingly, the protein once blocked by one or more amino groups does not provide a cause for the formation of an antibody as anti-original protein antibody even after the blocking amino groups have been eliminated.

Preparation of the Modified Carrier Protein

The process for preparing the modified carrier protein, according to this invention, will now be described with reference to the appended drawing.

Figure 1A:
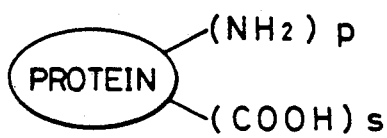
Figure 1A:
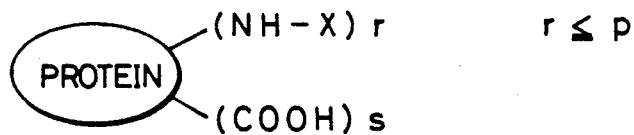
Figure 1A:
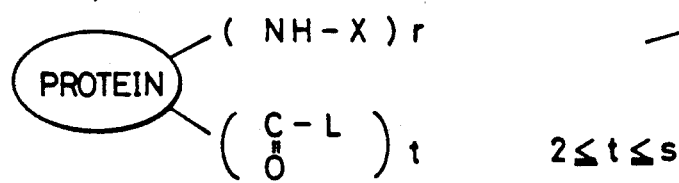
Figure 1A:
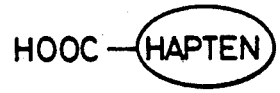
Figure 1A:
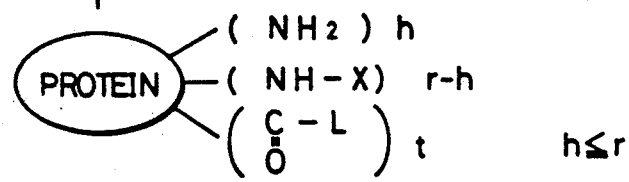
Figure 1B:
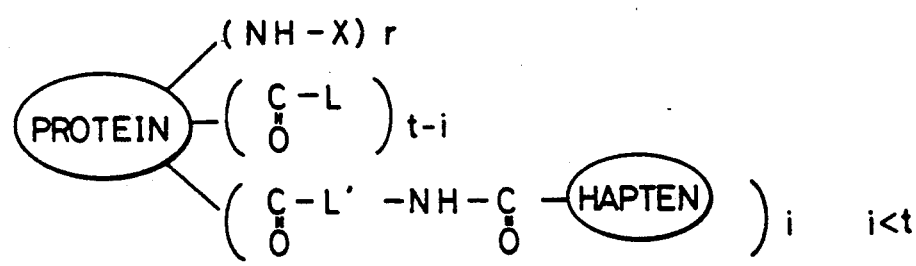
Figure 1B:
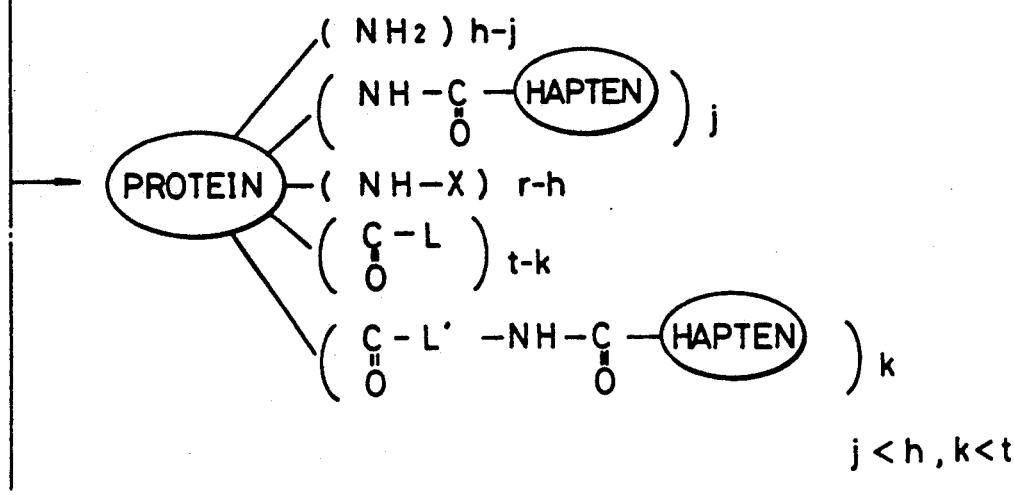

Referring to the flow chart of FIG. 1, the amino group of the original protein is blocked by an eliminable modifying group under a gentle condition (Step 1). When an urethane type modifying group is used, the amino group may be blocked substantially completely under a weakly alkaline condition while using several times the molar equivalent of the modifier.

The carboxyl group of the original protein is then converted into an amide group using a diamine or polyamine (Step 2). Methylenediamine, ethylenediamine or trimethylenediamine or other suitable diamines may be used as the diamine modifier, and diethylenetriamine or triethylenetetramine or other suitable polyamines may be used as the polyamine modifier. The carboxyl group of the original protein is activated by carbodiimide prior to the reaction, and a large excess amount of diamine or polyamine is added, the amount of the added diamine or polyamine being adjusted such that intramolecular and intermolecular cross-linking is substantially obviated.

Since the amino group of the original protein has been blocked substantially completely by the Step 1, intramolecular or intermolecular cross-linking reaction does not take place during the activation of carboxyl group at the Step 2. If the Step 2 is carried out without effecting the Step 1, the carrier protein would be polymerized by intramolecular cross-linking reaction to form an heterogenous protein mixture. The solubility of the resultant product in water is decreased considerably by such intramolecular or intermolecular cross-linking to make it difficult to carry out the subsequent operation of introducing hapten molecules. According to the present invention, disadvantageous intramolecular and intermolecular cross-linking are prevented to produce a homogeneous modified protein carrier which has satisfactory solubility in water.

In the resultant modified protein carrier, almost all of the amino groups of the original protein is blocked and thus the protein carrier has amino groups originated from the introduced diamine or polyamine.

Carboxyl groups of hapten molecules are combined with the introduced amino groups to obtain hapten-carrier conjugates (Step 4), and the thus obtained hapten-carrier conjugates may be used to immunize an immunorecipient animal. Not all of the introduced amino groups are combined with the hapten molecules, the number i of introduced hapten being less than the number t of the introduced amino groups and generally ranges not less than about 10.

When the modifying groups X are eliminated under a gentle condition (Step 3), the resultant modified protein carrier has the regenerated amino groups and the amino groups introduced by the Step 2. If protection of amino groups by the Step 1 and elimination of amino groups by the Steps 2 are effected, essentially perfectly, the number h of the regenerated amino groups is substantially equal to the number p of amino groups contained in the original protein so that the modified protein carrier has amino groups which are increased by number t of amino groups introduced into the carboxyl group when a diamine is used, or increased by number which is multiplication of the number obtained by subtracting 1 from the number of amino groups of the used polyamine. As a result, the sites at which the hapten can be introduced are increased at the maximum extent, so that the hapten can be introduced at a higher efficiency. Thus, a hapten-carrier conjugate suited for forming an anti-hapten antibody and having a high titer can be prepared (Step 5).

In this case, not all of the amino groups of the carrier are combined with the hapten molecules, the number j of hapten molecules combined with the regenerated amino groups and the number k of hapten molecules combined with the introduced amino groups are less than the number h of the regenerated amino groups and the number t of the introduced amino groups. However, the number of hapten molecules (h+t) are larger than that introduced into the original unmodified protein and also larger than that introduced into the modified protein prepared by the Step 2 in which the amino groups of the original protein is kept blocked. Accordingly, the efficiency in introduction of hapten molecules is improved. The number of hapten molecules necessary for immunization is generally more than about 10 molecules/carrier, and this requirement is easily satisfied by the use of a modified carrier protein in which the hapten introduction sites are increased to the maximum extent.

The modified protein carrier of the invention may conveniently be used as a carrier for carrying plural hapten antigens (Ag) in the passive agglutination immunoassay since the characteristics of the original protein is denatured by the modifying reaction in the Step 1 to lose the antigenicity as that of the original protein. Thus, even when it is allowed to contact with a carrier carrying plural anti-hapten antibodies (Ab), the antibodies (Ab) do not combine with the carrier (Ag*) per se. Accordingly, there is no need of absorbing the antiserum (Ab) preliminarily by the carrier (Ag*) or using a different carrier.

The same may be said when the amino groups are regenerated by the Step 3. The structure of a low molecular weight peptide may be returned to the original structure by the elimination of the modifying groups. However, even if the modifying groups are eliminated, the structures of high molecular weight molecules, such as proteins or polypeptides, are not returned completely to the original form once they have been modified. The three-dimensional structures of such high molecular weight proteins and polypeptides are denatured by the modification reaction. Consequently, even if the regenerated amino groups are used for the sites at which hapten molecules are introduced, an antibody for the carrier per se is not formed different from the case where an unmodified protein is used as the carrier.

According to a first aspect of this invention, amino groups of a protein are blocked by eliminable or uneliminable modifying groups and the carboxyl of the original protein is converted to amide form by using a diamine, polyamine or a polyamino acid to introduce additional amino groups. As a result, the amino groups of the original protein is completely blocked or decreased to modify the protein at high degree so that formation of the antibody (Ab*) for the carrier protein per se is substantially eliminated.

When a polyamine is used to block the carboxy group of the original protein, two or more amino groups are introduced to increase the sites at which hapten molecules are introduced, whereby the efficiency in introduction of hapten is improved.

By the use of the modified protein carrier of the invention, an anti-hapten antibody (Ab) can be efficiently prepared even if the available quantity of hapten is small.

The modified protein carrier of the invention may also be used in the passive agglutination immunoassay without the need of preliminary absorption of an anti-hapten antibody (Ab) by the carrier (Ag*) per se. A polyvalent haptens-antigens conjugate may be prepared by using the same carrier as used in the immunization operation.

According to the second aspect of the invention, the once blocked amino groups are deblocked so that hapten molecules can combined with the regenerated amino groups and also combined with the introduced amino groups. The number of sites at which hapten molecules are introduced is increased as compared with the unmodified protein and also as compared with the modified protein having amino groups blocked. The modified protein carrier has a high efficiency in introduction of hapten and may be used to prepare an antibody (Ab) even when the available quantity of hapten is very small. The modified protein carrier of the invention has a high degree of modification since the amino groups thereof have been once modified for protection purpose, so that it does not cause formation of antibody (Ab*) for the carrier.

EXAMPLE

The present invention will be described more specifically with reference to some Examples.

Example 1-1: Preparation of Acetylated BSA

One gram of BSA (produced by Sigma Chemical Co.) was dissolved in 100 ml of a 50 mM phosphate buffer solution (pH 9), and 0.5 ml of acetic anhydride was dropwisely added to the solution while cooling the solution on an ice bath. The pH value of the solution was monitored during the dropwise addition, and kept at pH 9 by adding a 1N NaOH solution. After the completion of dropwise addition, the reaction was continued at room temperature for 30 minutes under agitation. The reaction solution was subjected to gel filtration and desalting by flowing the same through a Sephadex G-10 column (produced by Pharmacia Finechamicals Co, Ltd.) equilibrated with a 1% acetic acid to separate the acetylated BSA. The yield of the lyophylized product was 1.05 g. The number of residing amino groups after the acetylation reaction was determined while using fluorescamine (produced by F. Hoffman la Roche) to find that the number of residing amino groups was about 0.1% of that of the BSA prior to the acetylation reaction.

Example 1-2: Introduction of Amino Group into Acetylated BSA

Amino groups were introduced into the acetylated BSA by condensation reaction between the carboxyl groups of the acetylated BSA and ethylenediamine.

One gram of the acetylated BSA prepared by Example 1-1 was dissolved in 50 ml of a 50 mM phosphate buffer solution (pH 8), and 5 ml of a 5% aqueous solution of a water-soluble carbodiimide (1-ethyl-3-(3-dimethylaminopropyl)-carbodiimide) was dropwisely admixed to the solution while cooling the solution on an ice bath, whereby the carboxyl groups of the acetylated BSA were activated. The admixture was dropwisely added to 50 ml of a 50 mM aqueous solution of ethylenediamine (PH 8) while stirring and cooling the solution with ice. After continuing the reaction for an hour at room temperature, the reaction mixture was subjected to gel filtration and desalting while using the Sephadex G-10 column similarly as in Example 1-1 to separate the reaction product which was then lyophylized to obtain a sample product. The number of introduced amino groups of the sample product was determined using fluorescamine to find that the number of introduced amino groups was about 60/one molecule of BSA. These amino groups were originated from ethylenediamine introduced into the carboxyl groups.

Example 1-3: Coupling of Hapten to the Modified BSA and Preparation of Antibody

1-Carboxybutyl-phenobarbital was used as a hapten so that it was coupled to the modified BSA.

100 mg of the modified BSA prepared by Example was dissolved in 10 ml of a 50 mM Tris-HCl buffer (pH 9). Separately, 100 mg of 1-carboxybutylphenobarbital was dissolved in 5 ml of dimethyl sulfoxide and added with 1.1 equivalents of triethylamine and 1.1 equivalents of isobutylchloroformic acid to form a mixed acid anhydride. The mixed acid anhydride solution was added to the solution of modified BSA to activate the modified BSA. After reacting at 4° C. for 30 minutes and then reacting at room temperature for an hour, the reaction solution was dialyzed to a flowing water for desalting purpose. The phenobarbital introduction quantity of the lyophylized sample was determined by the ultraviolet ray absorption spectrometry (measurements were conducted at wavelengths of 280 nm and 300 nm) The phenobarbital introduction quantity was so high as 45 moles/molecule of BSA.

The thus prepared modified BSA carrying hapten was inoculated to a rabbit to immunize the rabbit by the conventional method to obtain anti-phenobarbital sera of high titer.

The thus obtained anti-phenobarbital serum could be used for the passive agglutination immunoassay without the need of absorbing the modified BSA described in Example 1-2.

Example 2-1: Preparation of BSA Modified with Boc

Amino groups of BSA were blocked by modifying BSA with t-butoxycarbonyl (Boc) by the mixed-carbonate method.

One gram of BSA (produced by Sigma Chemical Co.) was dissolved in 100 ml of a 50 mM phosphate buffer solution (pH 9) and added with 0.6 ml of triethylamine and further added dropwisely with 50 ml of a 2% solution of t-butyl(4,6-dimethylpyrimidyl-2-thiol)carbonate (produced by Aldrich Corp.) in dioxane. After reacting for one overnight at room temperature with stirring, the reaction was stopped by the addition of 100 ml of water. The unreacted carbonate was removed by extracting with ethyl acetate, and then the water phase was dialyzed to flowing water for desalting purpose. The yield of the lyophylized BSA blocked by Boc was 1.08g. The number of residing amino groups was determined while using fluoscamine to find that the number of residing amino groups was less than 0.1% of that of the unblocked BSA.

Example 2-2: Introduction of Amino Groups into BSA Blocked by Boc

Amino groups were introduced into the BSA blocked by Boc by condensation reaction between the carboxyl groups of the blocked BSA and ethylenediamine.

One gram of the BSA blocked by Boc, as prepared by Example 2-1, was dissolved in 50 ml of a 50 mM phosphate buffer solution (pH 8) an added dropwisely with 5 ml of a 5% aqueous solution of a water-soluble carbodiimide (1-ethyl-3-(3-dimethylaminopropyl)carbodiimide) while cooling on an ice bath, whereby the carboxyl groups of the BSA blocked by Boc was activated. The solution was then dropwisely added to 50 ml of a IM aqueous solution of ethylenediamine (pH 8) while cooling on an ice bath to mix and react the former with the latter. After reacting at room temperature for an hour, the reaction solution was dialyzed to a flowing water for desalting purpose and then the reaction product was lyophylized. The number of the introduced amino groups in the sample product was determined while using fluorescamine to find that the number of introduced amino groups (originated from ethylenediamine) was about 60 per one molecule of BSA.

Example 2-3: Coupling of Hapten to the Modified BSA and Preparation of Antibody 1-Carboxybutyl-phenobarbital was used as a hapten which was coupled to the modified BSA blocked by Boc.

Generally following to the procedure as described in Example 1-3, 1-carboxybutyl-phenobarbital was coupled to 100 mg of the modified BSA prepared by Example 2-2. The quantity of introduced phenobarbital was so high as 43 moles per one molecule of the modified BSA.

The thus prepared modified BSA carrying hapten was inoculated to a rabbit to immunize the rabbit by the conventional method to obtain anti-phenobarbital sera of high titer.

Example 3-1: Elimination of Protection Group Blocking the Amino Groups of Modified BSA 500 mg of the modified BSA prepared by Example 2-2 was dissolved in 50 ml of a mixture of hydrogen bromide and glacial acetic acid to react at room temperature for 20 minutes. After the completion of reaction, the solvent was distilled off under a reduced pressure. After adding 100 ml of water, the reaction mixture solution was dialyzed to flowing water for desalting purpose and then the reaction product was lyophilized. The yield of the product was about 440 mg. The number of amino groups was determined while using fluorescamine to find that about 120 amino groups were introduced per one molecule of BSA. Since the number of amino groups of the blocked BSA prepared by Example 2-2 was about 60 per one molecule of BSA, it was found that 60 (20–60) amino groups per one molecule of BSA were regenerated.

Example 3-2: Coupling of Hapten to the Modified BSA Having Regenerated Amino Groups and Preparation of Antibody Similarly as in Example 2-3, 1-carboxybutyl-phenobarbital was coupled to 100 mg of the modified BSA having regenerated amino groups and prepared by Example 3-1. 65 moles/one BSA molecule of phenobarbital were introduced. This result was higher than the quantity of introduced phenobarbital (43 mols/one BSA molecule as described in Example 2-3) coupling to the modified BSA which is not subjected to the step of deblocking.

The thus prepared modified BSA carrying hapten was inoculated to a rabbit to immunize the rabbit by the conventional method to obtain anti-phenobarbital sera of high titer.

Example 4-1: Introduction of Amino Groups into Acetylated BSA

Amino groups were introduced into the acetylated BSA by condensation reaction between the carboxyl groups of the acetylated BSA and ethylenediamine.

One gram of the acetylated BSA prepared by Example 1-1 was dissolved in 50 ml of a 50 mM phosphate buffer solution (pH 8), and 5 ml of a 5% aqueous solution of a water-soluble carbodiimide (1-ethyl-3-(3-dimethylaminopropyl)-carbodiimide) was dropwisely admixed to the solution while cooling the solution on an ice bath, whereby the carboxyl groups of the acetylated BSA were activated. The admixture was dropwisely added to a 50 mM aqueous solution of ethylenediamine (PH 8) while stirring and cooling the solution with ice. After continuing the reaction for an hour at room temperature, the reaction mixture was subjected to dialysis and desalting while using flowing water, followed by lypophylization. The number of introduced amino groups of the sample produce was determined using fluorescamine to find that the number of introduced amino groups was about 50/one molecule of BSA.

Example 4-2: Coupling to Hapten to the Modified BSA and Preparation of Antibody 1-Carboxybutyl-phenobarbital was used as a hapten which was coupled to the modified BSA.

Generally following to the procedure as described in Example 1-3, 1-carboxybutyl-phenobarbital was coupled to 100 mg of the modified BSA prepared by Example 2-2. The quantity of introduced phenobarbital was so high as 67 moles per one molecule of the modified BSA.

The thus prepared modified BSA carrying hapten was inoculated to a rabbit to immunize the rabbit by the conventional method to obtain anti-phenobarbital sera of high titer.

Example 5-1: Introduction of Amino Groups into BSA Blocked by Boc

Amino groups were introduced into the BSA blocked by Boc by condensation reaction between the carboxyl groups of the blocked BSA and ethylenediamine.

One gram of the BSA blocked by Boc, as prepared by Example 2-1, was dissolved in 50 ml of a 50 mM phosphate buffer solution (pH 8) an added dropwisely with 5 ml of a 5% aqueous solution of a water-soluble carbodiimide (1-ethyl-3-(3-dimethylaminopropyl)carbodiimide) while cooling on an ice bath, whereby the carboxyl groups of the BSA blocked by Boc was activated. The solution was then dropwisely added to 50 ml of a 1M aqueous solution of ethylenediamine (pH 8) while cooling on an ice bath to mix and react the former with the latter. After reacting at room temperature for an hour, the reaction solution was dialyzed to a flowing water for desalting purpose and then the reaction product was lyophylized. The number of the introduced amino groups in the sample product was determined while using fluorescamine to find that the number of introduced amino groups (originated from ethylenediamine) was about 55 per one molecule of BSA.

Example 5-2: Coupling of Hapten to the Modified BSA and Preparation of Antibody

1-Carboxybutyl-phenobarbital was used as a hapten which was coupled to the modified BSA.

Generally following to the procedure as described in Example 1-3, 1-carboxybutyl-phenobarbital was coupled to 100 mg of the modified BSA prepared by Example 5-1. The quantity of introduced phenobarbital was so high as 65 moles per one molecule of the modified BSA.

The thus prepared modified BSA carrying hapten was inoculated to a rabbit to immunize the rabbit by the conventional method to obtain anti-phenobarbital sera of high titer.

Example 6-1: Elimination of Protection Group Blocking the Amino Groups of Modified BSA 500 mg of the modified BSA prepared by Example 5-1 was dissolved in 50 ml of a mixture of hydrogen bromide and glacial acetic acid to react at room temperature for 20 minutes. After the completion of reaction, the solvent was distilled off under a reduced pressure. After adding 100 ml of water, the reaction mixture solution was dialyzed to flowing water for desalting purpose and then the reaction product was lyophylized. The yield of the product was about 440 mg. The number of amino groups was determined while using fluorescamine to find that about 115 amino groups were introduced per one molecule of BSA. Since the number of amino groups of the blocked BSA prepared by Example 5-1 was about 55 per one molecule, it was found that 60 (115-55) amino groups per one molecule of BSA were regenerated.

Example 6-2: Coupling of Hapten to the Modified BSA Having Regenerated Amino Groups and Preparation of Antibody Similarly as in Example 1-3, 1-carboxybutyl-phenobarbital was coupled to 100 mg of the modified BSA having regenerated amino groups prepared by Example 6-1. 83 moles/one BSA molecule of phenobarbital were introduced. This result was higher than the quantity of introduced phenobarbital (65 moles/one BSA molecule as described in Example 5-2) coupling to the modified BSA which is not subjected to the step of eliminating the groups blocking the amino groups of the original protein.

The thus prepared modified BSA carrying hapten was inoculated to a rabbit to immunize the rabbit by the conventional method to obtain anti-phenobarbital sera of high titer.

What is claimed is:

1. A modified protein for carrying a hapten represented by the formula:

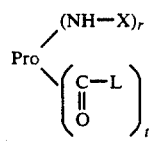

wherein
Pro is a protein or a polypeptide;
X is a uneliminable or eliminable modifying group for the amino group;
L is a substituted or unsubstituted alkyl group having 1 to 8 carbon atoms and three or more amino groups, one of which combines with the carboxyl group of Pro by an amide linkage;
r is an integer of from 1 to the number of amino groups in the unmodified Pro; and
t is an integer of from 1 to up to the number of carboxyl groups in the unmodified Pro.

2. The modified protein for carrying a hapten as claimed in claim 1, wherein said modifying group X is represented by the following of:

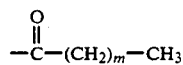

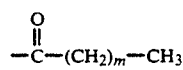

wherein m is an integer of from 0 to 4.

3. The modified protein for carrying a hapten as claimed in claim 1, wherein said modifying group X is selected from the groups consisting of:

—CO—O—R
$SO_2$—R
—CO—S—R
—S—R

—CHO
—CO—$CH_2$—$COCH_3$
—CO—$CF_3$
—$CH_2$—$C_6H_5$
—CH—$(C_6H_5)_2$, and
—C—$(C_6H_5)_3$, wherein R is a substituted or unsubstituted alkyl, aryl or arylalkyl group having 2 to 15 carbon atoms.

4. The modified protein for carrying a hapten as claimed in claim 1, wherein said modifying group X is represented by the following formula of:

—CO—Y—Z—R wherein Y is a substituted or unsubstituted methylene group; Z is sulfur or oxygen atom; and R is a substituted or unsubstituted alkyl, aryl or arylalkyl group having 2 to 15 carbon atoms.

* * * * *